United States Patent [19]

Lange

[11] Patent Number: 5,132,107

[45] Date of Patent: Jul. 21, 1992

[54] TWO-PHASE CLEANSING, CONDITIONING AND MEDICINAL TREATMENT SHAMPOO

[76] Inventor: Bouke J. Lange, P.O. Box 130; 2810AC, Reeuwijk, Netherlands

[21] Appl. No.: 590,050

[22] Filed: Sep. 28, 1990

Related U.S. Application Data

[63] Continuation of Ser. No. 163,824, filed as PCT/EP87/00372, Jul. 7, 1987, abandoned.

[30] Foreign Application Priority Data

Jul. 7, 1986 [NL] Netherlands .................. 8601762

[51] Int. Cl.$^5$ ............................................ A61K 7/075
[52] U.S. Cl. ................ 424/70; 424/DIG. 4; 514/852; 514/557; 252/106; 252/DIG. 13
[58] Field of Search ............... 424/DIG. 4, 70; 514/852, 864; 252/106, DIG. 13

[56] References Cited

U.S. PATENT DOCUMENTS

| | | | |
|---|---|---|---|
| 2,950,255 | 8/1960 | Goff ................................. | 424/70 X |
| 3,676,546 | 7/1972 | Ghilardi et al. ................... | 424/71 |
| 3,842,847 | 10/1974 | Hewitt et al. ..................... | 424/70 X |
| 4,185,106 | 1/1980 | Dittmar et al. ........... | 424/DIG. 4 X |
| 4,363,815 | 12/1982 | Yu et al. ................... | 424/DIG. 4 X |
| 4,430,250 | 2/1984 | Sebag et al. ..................... | 424/63 X |

FOREIGN PATENT DOCUMENTS 00041 1/1988 PCT Int'l Appl. .

OTHER PUBLICATIONS

Page 49 of the Hunting Article in Cosmetics & Toietries, vol. 100, Mar. 1985.
Pages 415, 425, and 426 of the Goldemberg article in J. Soc Cosmet Chem, 30, Dec. 1979.
Kligman article in Norda Briefs, Markland.

*Primary Examiner*—Thurman K. Page
*Assistant Examiner*—Neil S. Levy
*Attorney, Agent, or Firm*—Fleit, Jacobson, Cohn, Price, Holman & Stern

[57] ABSTRACT

Two phase shampoo allowing sequential application of substances/conditions, especially for controlling dandruff, wherein the first phase consists of a detergent composition, together with possible adjuvants, having a neutral or alkaline pH and the second phase, separated from the first phase, comprises a physiologically acceptable acid component, or mixture of such components, which phase is applied immediately after the treatment of the hair and the skin of the head with the first phase. Both phases may contain an antimycotic.

16 Claims, No Drawings

TWO-PHASE CLEANSING, CONDITIONING AND MEDICINAL TREATMENT SHAMPOO

This application is a continuation of application Ser. No. 07/163,824, now abandoned, filed Mar. 7, 1988, national phase of PCT/EP87/00372, filed Jul. 7, 1987.

The invention generally relates to a process for cleansing and conditioning (keeping in a good shape) of hair and skin of the head, within the context of periodically necessary hygienic, cosmetic or medicinal treatment of the hair and skin of the head.

The invention particularly relates to the control of dandruff and similar scale forming conditions of the skin of the head, as well as a two-phase shampoo for this purpose as well as a packing therefore.

The invention will now be described with the emphasis on the last variant but is not restricted thereto.

Although the etiology of dandruff is not yet completely elucidated there are strong indications that yeast infections, such as by pityrosporum yeasts play an important role. Although yeast cells like *Pityrosporum ovale* or *orbiculare* are normally found on the skin, some people do have dandruff while others don't. For the cleansing of the hair and scalp and the elimination of dandruff one normally uses a shampoo, which in general consists of a detergent and other components, which give certain properties to shampoo. The basic component is a detergent which by its fat solubilizing ability and the rinsability with water is able to cleanse the scalp and the hair. However, it is not possible to completely eradicate dandruff by such a shampoo. The flakes are indeed largely eliminated but after a relatively short period new dandruff scales are developing, possibly by the influence of microbial metabolic products (for example microbial toxins). The control by anti mycotics over longer periods of time involves disadvantages in connection with possible toxic contra-indications or the development of resistance by the dermatophytes. Equally, treatment with means to retard cell proliferation or cell division is not advisable, since the excessive corneocyte production and scaling is probably a consequence of pathogenesis resulting from the said infection process and not the cause of dandruff (see: The aetiology of dandruff and the mode of action of therapeutic agenst; S. Shuster; British Journal of Dermatology; 1984, 281, pages 235:242). It would be desirable if one could have at one's disposal a process and shampoo composition enabling one to combine the normal cleansing and conditioning of the hair and scalp with an effective method to eradicate dandruff, without making use of toxic and resistance-inducing anti mycotic or cytostatic substances.

The invention is intended to provide such a process as well as a shampoo composition by which control of dandruff and related scale forming conditions is possible without the complications mentioned.

It is known that by cleansing the hair and scalp with detergents (soaps, anionic and non-ionic detergents) the physiological and biological equilibrium of the epidermis and especially the natural pH (acidity) of the epidermis is affected (see: C. E. Orfanos-Haar und Haarkrankheiten, Gustav Fischer Verlag, 1979, especially page 955 and Biology of Hair, Tatsugi Kobori and William Montagna, 1975, page 598). The process and shampoo composition of the present invention is aimed at restoration of this equilibrium and a consecutive neutralisation of the potentially damaging effect of the cleansing procedure and dandruff control.

The invention now provides a process and associated shampoo composition by which the skin of the head and the hair is treated in two phases; on the one hand to cleanse, condition and/or control yeast growth as is shown in the main embodiment in the first phase and on the other hand for recovery and consolidation in the second phase of the equilibrium which is destroyed by the detergents etc. Both treatments are carried out separately and consecutively, but as will be understood carried out in a synergistic combination.

Thus the invention provides a process for treating the skin and hair, especially to control dandruff and similar scale forming conditions, whereby the hair is washed with a detergent composition and after rinsing out this is treated consecutively with a separately applicable composition with an acid pH in the absence of detergents, by which microbial growth is inhibited through both treatments.

In particular the hair is washed with a detergent composition containing a combination of non-irritating detersive materials as well as amphoteric materials counteracting irritation, if desired together with viscosity modifying materials as well as suitable substances to prevent dehydration of the skin by the detersive action (so called Rückfetter), whereby in the main embodiment an anti-mycotic is included, being a suitable water soluble anti-mycotic to induce dandruff control. As mentioned no such substances should be used which give rise to microbial resistance.

In the phase I composition one aims at a thorough cleaning of the hair and scalp combined with a skin condition promoting treatment. For this purpose substances are added which are beneficial to the skin, such as the mentioned "Rückfetter", as well as for instance amphoteric substances. It is to be understood that the phase I treatment is carried out under such circumstances and with such means (thorough cleaning, minimised skin irritation, weakly alkaline pH, as well as the onset of control of fungi) as to promote optimal effect of subsequent phase II treatment.

The invention also provides a two-phase shampoo comprising an integrated shampoo consisting of two compositions, wherein the phase I composition holds a detergent, together with possible cofactors, at a neutral or weakly alkaline pH, and the phase II composition separately from the phase I, comprising a physiologically acceptable acid component which composition is used consecutively, preferably immediately after washing out the phase I composition. Furthermore, the invention relates to a packaging, for the two-phase shampoo wherein the two compositions are integrated in one package.

To a limited extent shampoo compositions with an acid pH (for instance by including citric acid) are already known, but it has been found that soaps are not well suited for making lower pH products (Cosmetics & Toiletries, volume 95, May 1980, page 79). Thus the simultaneous action of the two previously mentioned compositions included in one shampoo is practically not feasable.

It is assumed that the substance of the corneum (the protein keratin) through a normal alkaline shampoo obtains a "woolly" stereochemically open surface structure, which is advantageous for cleansing but also promotes reinfections and/or growth of established skin flora. This has as a consequence for instance that dandruff is quickly reestablished and is returning regularly irrespective of the treatment with such a shampoo.

It has been found that by a subsequent second treatment with an acid rinsing liquid surface proteins of the skin can be made to coagulate by which they obtain a "closed" stereochemically densely clustered structure (among others as a consequence of the formation of hydrogen bridges); at the same time a more natural pH is obtained. By this one achieves that renewed formation of dandruff etc., which amongst others would be promoted by the open skin structure induced by the alkaline detergent, can be counteracted by the second treatment while also by the acid pH the growth of the head skin flora is further inhibited and irritation reduced. Several organic acids are used in a dilute solution for various dermatological purposes in view of their antiseptic action. It is further postulated that amongst others the acid component in the phase II treatment penetrates through the pores into the epidermis and absorbed in the skin cells participates with the normal cell metabolism and gives the contemplated favourable biochemical effect. One thus can state that by the phase II treatment the following is reached: 1. an astringent and anti-irritation effect (stereochemical surface-effect), 2. a biochemical stimulating effect on cellular level after absorption of the component and participation with the intracellular metoblism, and 3. the antiseptic effect of the acid (which is known per se). See in this connection Dermal and Transdermal Absorption, Rainer Brandau, Bärbel H. Lippold, Wissenchafliche Verlaggesellschaft m.b.h., Stuttgart, 1982, page 31 and 35 and the Molecular Biology of Skin, P. Mier Ph.Dr., J. D. Cotton, Ph.D., Blackwell 1976, page 57, and "Cosmetics & Toiletries", volume 100, No. 3 (1985), page 52, Shampoo documentary.

The phase I composition essentially consists of a detergent, such as normally used in shampoos, selected from the various anionic, cationic, non-ionic or amphoteric detergents and in such a formulation that it is not harmful to the skin. For a survey of these means one is referred to the Handbook of Schwarz, Perry and Berch, Surface Active Agents, published 1958 by Interscience Publishers and in McCutcheon's Detergents and Emulsifiers, 1969 Annual.

In principle any physiologically acceptable, mild detergent, which does not have a directly damaging effect (for instance sensibilisation or toxicity) on the skin or causes damage to the hair and which possesses sufficiently cleansing and dissolving power, is used. Mild detergents in combination with protein condensation products, hydrolysates etc., such as these are commercially available, are preferred.

Good examples are amongst others blends of laurylether sulphate, laurylpolyglycolether sulphosuccinate and fatty acid alkylamides (commercially available as Rewopol (R) of REWO.)

The pH of the phase I composition (also including mixtures, combinations and formulations) is preferably in the neutral or weakly alkaline range. The best results are obtained with a pH between 7.5 and 8.5, but preferably not above 8.5, always with the condition that the activity is physiologically acceptable. The purpose is to further an open structure of the epidermis, as mentioned above, thus enhancing the permeability of the epidermis, so that a detergent, antimycotic or conditioning agent may be used optimally.

Phase I formulation may be a solution, emulsion or suspension, (such as is commonly used for shampoos) whereby the consistency may be adjusted by viscosity modifying agents. A good detergent power and a good rinsability is prime objective.

In phase I formulation a conditioner may be included, by which the hair can be brought in such a condition that the phase II treatment has a better cosmetic effect. Gelatin, casein, keratinous compounds, such as albumin proteins, which are physiologically acceptable are preferably used. It has been found that using these substances a thin protein layer remains on the skin and the hair which contributes to the protective effect of the acid treatment as indicated in the beginning.

Examples of the keratinous materials are albumins, such as amongst others lactalbumin and ovalbumin and possibly vegetable matters of that kind. These substances are included in sufficient amounts to obtain the desired effect; normally this amounts to a few percent, for example 0.5–7.5 percent by weight of the phase I mixture.

In some cases it is advantageous to make use of the open structure of the skin caused by the phase I treatment through an alcohol to further penetration of effective anti-mycotics into the skin and thus to potentiate phase II action.

Also this possibility is of importance in using particular organic acids in the phase II composition, which acids per se possess an anti microbial action, such as fumaric acid and azelaic acid. In this way the effect of the antimycotic in phase I as well as phase II is enhanced!

The phase I composition may contain anti-mycotics in the medicinal as well as the anti-dandruff variant, provided these do not induce resistance as mentioned above. One may use an anti-mycotic substance in combination with albumin or a protein condensation product. An example of such anti-mycotic substance is tar, especially tar soap. Furthermore, anti-mycotics like zinc pyridithion, sulfur and lithium compounds (see British Medical Journal 292, January 1986, page 28) imidazole derivatives (compounds) are acceptable as long as they are used in physiologically acceptable concentrations. Of course one may also use general pharmaceutics, provided these display a softening or irritation lowering effect.

In a specific embodiment on may use a water soluble anti-mycotic such as piroctone olamine (Hoechst), chemical name 1-hydroxy-4-methyl-6-(2,4,4-trimethylpentyl)-2-(1H)-pyridinone compound with 2-aminoethanol (1:), whereby as mentioned above, the effect in phase I as well as phase II treatment (if carried out with "quats" in the phase II composition), can be optimalized. The amounts thereof are resp. between about 1% and 0.2% preferably 1,0% and 0,3% (%, based on weight of mixture). One may also use zinc pyridithion in which case it is recommended to use a mixture with disòdium undecylenic acid monoethanol amidosulfosuccinate (Rewocid (R) of REWO) which as is known forms a synergistic mixture with zinc pyridithion. Rewocid, the said undecylenic acid derivative as such is useful as well as other sulfosuccinates in phase II as a antimicrobial substance which has a mild effect on the skin, and thus contributes to the control of dandruff.

The phase I composition preferably contains a pH-stabilizer like a pH buffer, by which one achieves that the action as desired by the phase I composition is secured, i.e. the cleaning and rinsing effect as well as the conditioning effect. The advantage of the pH adjustment by means of a buffer of the phase I composition in the alkaline range is that the above action of the detergents can be optimized without damaging side effects (for example extreme alkalinity).

Phase I composition may furthermore contain adjuvants and other additives which are usual for shampoos such as thickeners, preservatives, anti-oxidants, dyes, flavouring agents, opacity promoting, clarifying or sequestrating agents as well as foam controlling agents; in the amounts which are usual for these adjuvants. However, it is preferred to use as little as possible of these substances and to balance the compositions within the presently established dermatological limits (see Orfanos Supra) as indicated by our objectives.

The phase II composition contains a solution of a physiologically acceptable organic acid or mixture of these acids. An acid is preferred which participates in the normal cell metabolism. These acids may be saturated or unsaturated, mono or poly basic, especially dibasic organic acids, preferably with 2-16 carbon atoms (branched of linear) which may be subsituted with acceptable substituents, like for instance especially the alpha-hydroxy acids. The acids may contain aromatic substituents.

Examples of these acids are acetic, propionic, fumaric, benzoic, maleic, azelaic, citric, salicylic, succinic, pyruvic, glutaric, malic, lauric, malonic, lactic, undecenic, undecylenic, decane-1, 10-dioic acid and derivatives thereof. Organic acids which are known to give a therapeutic effect in the treatment of skin deceases have preference, like fumaric, azelaic, decane-1, 10-dioic, salicylic, acetic, propionic, benzoic, undecylenic, sorbic acid etc.

The acidity of the phase II solution is generally adjusted in the area of pH 3-6, preferred 4-5. The acidity of the phase II composition is adjusted in such a way that after application a situation is reached which is as much as possible in agreement with the natural pH of the skin. This means that since pH regulation takes place on the scalp by biochemical buffer action etc., preference is given to a pH which is slightly below the physiological value, which pH after use of the two phase treatment is adjusted upward to the physiological value. See for this matter Rainer Branday as already mentioned, page 35.

The phase II composition may further contain adjuvants which promote the action of the phase I composition. As such, well known astringents can be cited, which reinforce the action of the acids and are physiologically acceptable, like aluminium and zinc salts (for example alum and tanning agents like tannin). Also epithelium growth promoting substances may be applied like dexpanthenol.

One may further include anti-septic or disinfectant substances, as well as anti-mycotics which are known per se, in so far as these are not taken up in the phase I composition for chemical reasons, like for example undecylene derivative products. Also adjuvants may be utilized like for instance for protective means, epidermal reinforcement or nurturing, cosmetic means, which also includes the usual colouring and flavouring substances, as well as hair growth stimulating means, like minoxidilum.

One may also use piroctone olamine in phase II because of its anti-seborrhoeic effect. When this is combined with an organic acid with antiseptic properties one obtains an enhanced broad spectrum activity which is of importance because of the relatively short period of duration of a shampoo rinsing treatment compared with a long lasting therapy.

It will be understood that also cosubstances are desired which sustain as much as possible the action contemplated and contribute cosmetically to attractive properties as well. E.g. it is preferred to use as solvent a mixture of water and alcohol which gives a good percutaneous absorption and strengthen the effect of the acid and the antimicrobial agents. Also thickeners can be added, like tylose (hydroxyethyl cellulose) and similar cellulose derivatives.

Thus with the rinsing liquid a pH restoration and hydrogen bonding of the epidermal layer proteins is reached as well as the proteins supplied by means of formulation I, so that a protective action occurs and also a sebo suppressive effect is obtained by which a continued action of pityrosporum yeast are inhibited. The two formulations of the two-phase shampoo are used in combination and they are suitably packed together but separately, on the one hand because both compositions may not be mixed without loss of effectivity and on the other hand because the synergistic effect of the components used in both liquids is only obtained if they are used one directly after the other! The effect of the phase II formulation thus is only reached when used consecutively and almost directly after the cleansing treatment and water rinsing, but before the head skin flora can recover. After the application of the phase II formulation, as is the case after phase I, rinsing takes place with water. Through transdermal absorption, however, the phase II composition and its effects on the scalp is maintained sufficiently till the next shampoo treatment, while the excess of components from this formulation on the skin surface is eliminated by rinsing with water so that also from a cosmetical point of view one has reached a better hair- and skin condition.

The invention thus also comprises packaging modifications wherein both components of the two-phase shampoo are taken up separately but combined in one package. a suitable embodiment is amongst others a plastic container, provided with two juxta positioned flasks, which container also may be provided with a plastic plate to connect it with an adhesive strip against the wall of the bath room. Both flasks can be separately packaged or for convenience be esthetically combined. For this last purpose one flask in another embodiment is used which contains a separating wall by which two compartments are formed. One may also provide a combined moving or flip opening, or another type of opening, by which firstly the compartment with the detergent (phase I) can be dispensed and thereafter the compartment with the rinsing liquid (phase II). Preferably the container or compartments are distinguished from each other by size, appearance or other sensory effect (color, consistency, etc. of the components).

EXAMPLE 1

Shampoo for psoriasis-like seborrhoic dermatitis*

*Shuster (1984) Br. J. Dermatol. 111, page 235

With a medicinal variation of the two-phase shampoo a treatment was carried out using test persons during several months, wherein two times a week the hair was washed. The test persons were persons suffering from tenacious dandruff, while one of them suffered from a grave seborrhoeic dermatitis. As a first component of the two-phase treatment one used for this purpose the following composition:

|  | percentage |
|---|---|
| Triethanolamine laurylsulphate (detergent) | 45 |
| glycerine (clarifyer and conditioner) | 5 |
| lauryldiethanolamide (foam booster) | 5 |
| buffer and sequestrating agent | 0.2 |
| coal tar distillate (Fluxöl ST) | 1.5 |
| colouring and perfume with water | to 100% | pH is in the weakly alkaline domain. Fluxöl ST (commercial product) is used because besides its antimycotic action it also has a keratostatic and sebosuppressive action (in the second phase of the treatment the weak tar smell was almost neutralized).

The phase I composition of the two-phase shampoo was supplied on the wet scalp in the normal way and rubbed in.

By means of the composition of this first phase of the scalp-treatment, the deeper resident microflora is reached through the fat dissolving action of the detergent, by which the dermatophytes in the hair follicle and sweat gland pores are eradicted more effectively via the antimycotic action of coal tar destillate.

Thereafter the composition was as usual rinsed out with water. Immediately thereafter in the second phase a head skin-treatment was carried out with a composition with a low pH which for this experiment was formulated as follows:

| dexpanthenol | 2% | (epithelium growth promoting factor) |
|---|---|---|
| fumaric acid | 5% | (anti-psoriasis factor) |
| ethanol | 15% | (desinfectant) |
| Al-acetate tartrate | 0.2% | (astringent) |
| lanoline | 0.2% |  |
| hydroxypropylcellulose | 1% | (gelling agent) |
| flavour and colouring materials water | to 100% |  |
| pH about 3.5 |  |  |

With this composition complete freedom of the seborrhoic constitution was effected and in combination with phase I treatment in due course an effective eradication of the pityrosporum fungus on the head was reached. An exposure time of about 2 minutes in the second phase was sufficient. This was followed by rinsing with water. The epithelium-promoting, antiseptical, pH reducing and astringent effect of this treatment on the scalp persists by transdermal absorption in the epidermis through pores and corneocytes to a sufficient degree till the next shampoo treatment.

It thus appears that with this two-phase shampoo of the invention already after several weeks an effective control of seborrhoeic dermatitis and dandruff was obtained.

EXAMPLE II (Conditioning Anti-Dandruff Shampoo)

One starts from a phase I composition in the cosmetic variation with zinc pyridithion as anti-mycotic.

|  | Percentage |
|---|---|
| Cocoamphocarboxyglycinate | 15 (amphoteric) |
| Cocoamidepropyl hydroxysulfobetaine | 10 (amphoteric) |
| Sodium lauryl sulphate | 15 (detergent) |
| Lauramide DEA | 1 (foam booster) |
| Cocamine oxyde | 1 (foam booster) |
| Zinc pyridithion (48% dispersion) | 3 (anti-mycotic) |
| Polyquaternium 17 (Mirapol AD-1) | 2 (conditioner) |
| Water, colour and flavour to | 100% |
| pH adjusted to 7.8 |  |

The phase II composition contains an alpha-hydroxy-acid like lactic acid which plays an important physiological role in the structural stability and functional elasticity of the epidermis and keratine proteins.

|  | Percentage |
|---|---|
| Allantoine | 2 (cosmetic epithelium growth promoting agent) |
| lactic acid | 5 (bacterio and mycostatic agent) |
| Negatol | 30 (astringent) |
| Methylcellulose | 1 (gelling agent) |
| Flavouring and colouring materials water to | 100% |
| pH to 4.5 with NaOH |  |

The results in this treatment of dandruff were comparable with those of example I; a sound skin with retention of biologically and cosmetically favourable hair properties was obtained.

Similar or even better results were obtained when substituting piroctone olamine for zinc pyridithion (the effective amount of the first is about half of the amount of the latter). It also appears that by having a small amount of quaternary ammonium compounds ("quat") present, the retention of the anti-mycoticum on the skin is enhanced.

EXAMPLE III

One started with a clear phase I shampoo composition which was specifically formulated to possess in addition to anti-dandruff action also good foaming and conditioning properties.

|  | Percentage |
|---|---|
| Cocoamidopropylbetaine | 20 (amphoteric) |
| Sodium laurylsulphate | 25 (detergent) |
| Cocodiamoniumcollagene hydrolysate | 1 (protein conditioner) |
| Acetamide MEA | 1 (conditoner) |
| Lithiumsuccinate* | 5 (anti-mycotic) |
| Propylene glycol Propylene paraben Methyl paraben | 1 (preserving agents) |
| Flavouring and colouring materials water to | 100% |
| pH 7.5 |  |

*British Medical Journal (1986) 292,28 "Use of topical lithium succinate for seborrhoic dermatitis".

The phase II composition was formulated according to example I with the exception that fumaric acid was replaced by dodecanedioic acid 8%. The results were comparable.

EXAMPLE IV

One formulated an eggwhite shampoo as phase I composition as follows.

|  | Percentage |
| --- | --- |
| Sodiumlaurylthiosulphate keratine complex (this detergent also has an anti-dandruff action) | 5% |
| Triethanolamine laurylsulphate | 10.5% (detergent) |
| Laurylisopropanolamide | 1.5 (conditioner) |
| Methylparaben | 1 (preserving agent) |
| pH 7.5 | |

The phase II composition was formulated according to example I with the exception that fumaric acid was replaced by azelaic acid 5%**. Here also a favourable anti-seborrhoic effect was obtained.

** Ref. British Journal of dermatology (1986), 114,493.

EXAMPLE V

One started from a phase I composition which contained acylated sodium laurylsulphate (20%), as detergent and cocodiethanolamide and anhydrous lanolin (both 0.6%). Furthermore 1% albumin was included as conditioner. In composition I also 1% zinc pyridithion was present with the remainder water. The pH was above 7.5. The phase II composition was 5% acetic acid with, 30% ethanol, thickening agents, flavouring and colouring materials. During regular use a lasting curative effect was obtained which was promoted by the albumin conditioning agent.

EXAMPLE VI

The experiment of example I was repeated, however, the phase I anti-fungus component was Omadine 1,5%. Also an effective control of dandruff was obtained.

EXAMPLE VII

The two-phase shampoo of examples I–VI was held in a carrier fixed to the wall provided with two recesses, in which the respective flasks for compositions I and II fitted, whereby the flask of composition II was congruent with flask I, but larger and with another appearance. The container was connected to the wall by means of an adhesive strip so that one could easily carry out the two-phase treatment.

EXAMPLE VIII

The two-phase shampoo of examples I–VI was presented in one flask provided with a compartment-forming separating wall and two flip openings through which compositions I and II could easily and in the right order be delivered from the flask. As in example VII the two-in-one flask was provided with a handy plateau, which could be connected to the wall by means of an adhesive strip.

I claim:

1. A process for the medicinal treatment of the scalp to control dandruff and other related conditions, comprising:
   washing the scalp in a first phase with a first phase-treatment composition which includes a non-irritating detergent and an anti-mycotic at a pH which is neutral or alkaline;
   rinsing out the first phase-treatment composition; and
   treating the scalp with a second phase-treatment composition comprising an hydrophilic alcohol gel and a physiologically acceptable organic acid at a pH of 3–6 immediately after the rinsing out of the first phase-treatment composition.

2. The process according to claim 1, wherein the first phase-treatment composition also includes a non-irritating amphoteric substance and a skin moisturizer for counteracting drying out of the skin due to excessive defatting.

3. The process according to claim 1, wherein the anti-mycotic used in the first phase is a water-soluble anti-mycotic and the acid used in the second phase comprises an organic acid with an anti-microbial action.

4. A two-phase dandruff medicinal shampoo, comprising, in combination:
   a first phase-treatment composition which includes a non-irritating detergent and an anti-mycotic at a pH which is neutral or alkaline;
   a second phase-treatment composition, for use immediately after the first phase-treatment composition after rinsing out the first phase-treatment composition, comprising an hydrophilic alcohol gel and a physicologically acceptable acid at a pH of 3–6; and
   wherein the first and second phase-treatment compositions are physically separated from each other.

5. The shampoo according to claim 4, wherein the first phase-treatment composition further includes a non-irritating conditioning substance and a non-irritating amphoteric substance and a skin moisturizer for counteracting drying out of the skin due to excessive defatting.

6. The shampoo according to claim 4, wherein the first phase-treatment composition contains a buffer.

7. The shampoo according to claim 4, wherein the pH of the second phase-treatment composition is in the range of 4 to 6.

8. The shampoo according to claim 7, wherein the pH of the second phase-treatment composition is about 5.

9. The shampoo according to claim 4, wherein the second phase-treatment composition includes an anti-mycotic.

10. The shampoo according to claim 9, wherein the anti-mycotic contained in the first phase and the second phase-treatment compositions is a water soluble anti-mycotic of the type that does not incur dermal and systemic toxicity and microbial resistance phenomena.

11. The shampoo according to claim 4, wherein the acid component comprises an organic acid having a chain length of 2 to 15 carbon atoms and is selected from the group consisting of a branched acid, a saturated acid, an unsaturated acid, an acid substituted with an aromatic group and di-or polyvalent acids.

12. The shampoo according to claim 4, wherein both the first phase-treatment composition and the second phase-treatment composition include a dexpanthenol and linoleic acid diethanol amide.

13. The shampoo according to claim 4, wherein the first phase-treatment composition has a pH in the range of 7.5 to 8.5.

14. The shampoo according to claim 4, wherein the first phase-treatment composition contains a keratolytic agent.

15. The shampoo according to claim 9, wherein the anti-mycotic in both the first phase and the second phase-treatment compositions comprises piroctone olamine.

16. The shampoo according to claim 15, wherein the acid in the second phase-treatment composition comprises azelaic acid.

* * * * *